(12) United States Patent
Grubb

(10) Patent No.: US 9,782,288 B2
(45) Date of Patent: Oct. 10, 2017

(54) ADJUSTABLE URINARY CATHETER FASTENER

(71) Applicant: Lisa Grubb, Elkridge, MD (US)

(72) Inventor: Lisa Grubb, Elkridge, MD (US)

( * ) Notice: Subject to any disclaimer, the term of this patent is extended or adjusted under 35 U.S.C. 154(b) by 124 days.

(21) Appl. No.: 15/044,508

(22) Filed: Feb. 16, 2016

(65) Prior Publication Data

US 2017/0231803 A1   Aug. 17, 2017

(51) Int. Cl.
*B25B 1/00* (2006.01)
*A61F 5/44* (2006.01)

(52) U.S. Cl.
CPC .................. *A61F 5/4408* (2013.01)

(58) Field of Classification Search
CPC .... B25B 1/02; B25B 1/00; B25B 3/00; B25B 5/00; B25B 5/025; B25B 5/108
See application file for complete search history.

(56) References Cited

U.S. PATENT DOCUMENTS

| | | | |
|---|---|---|---|
| 3,384,935 A | 5/1968 | Salvador | |
| 4,833,759 A | 5/1989 | Larsen | |
| 4,926,722 A | 5/1990 | Sorensen et al. | |
| 4,987,660 A | 1/1991 | Sagucio | |
| 5,154,398 A * | 10/1992 | Mayfield | B25B 27/30 254/10.5 |
| 5,584,458 A * | 12/1996 | Rando | F16M 13/022 248/206.5 |
| 6,266,854 B1 | 7/2001 | Ancona et al. | |
| 6,438,854 B1 * | 8/2002 | Kott, Jr. | B25B 5/068 269/6 |
| 6,530,565 B1 * | 3/2003 | Simpson | B25B 5/166 269/147 |
| 6,658,711 B1 * | 12/2003 | Benson | B25B 5/068 269/3 |
| 6,813,814 B1 | 11/2004 | Schultz | |
| D526,559 S | 8/2006 | Lewis | |
| 7,168,181 B2 * | 1/2007 | Walchak | B25B 5/068 269/36 |
| 7,484,310 B2 * | 2/2009 | Jaffers | B25B 5/003 269/143 |
| 7,546,996 B2 * | 6/2009 | Somji | F16M 11/045 248/229.14 |
| 2015/0246431 A1 * | 9/2015 | Shute | B25B 5/163 144/195.4 |

* cited by examiner

*Primary Examiner* — Lee D Wilson
(74) *Attorney, Agent, or Firm* — Larry J. Guffey, Esq.; Pamela K. Riewerts, Esq.; Oliver & Grimsley, LLC

(57) ABSTRACT

An adjustable fastener for a urinary catheter bag includes a slide bar, a movable jaw attached to the slide bar, a grip assembly having a passageway that is adapted to accommodate the slide bar, a fixed jaw affixed to the grip assembly, a biasing assembly attached to the grip assembly and slide bar in such a manner so as to apply a prescribed biasing pressure between the jaws to temporarily adhere them to a structural member in the vicinity of a patient who is using the catheter bag, and a hook that is pivotably attached to an end of the slide bar and configured to set the angular orientation of the hook so that the secure hanging of the catheter bag from the fastener is promoted.

20 Claims, 4 Drawing Sheets

ADJUSTABLE URINARY CATHETER FASTENER

BACKGROUND OF THE INVENTION

1. Field of the Invention

The present invention generally relates to connectors or clamping devices, and specifically, to an adjustable fastener for a urinary catheter bag that attaches the bag to any one of a multitude of structural members in the vicinity of the one who is using the bag.

2. Description of the Related Art

Urinary catheter devices are widely used in the health care industry. Typical urinary catheters include a flexible catheter drainage tube that is connected to a urinary discharge or catheter bag which collects the urine as it is passed by the patient. These bags are typically made of clear or transparent materials on one side so that the contents of the bags can be readily observed. When in use, they are typically hung from objects or structural members in the vicinity of the patient so that the bag's longitudinal centerline is oriented vertically so as to use gravity to assist in the bag's collection process.

There are quite a few restrictions on how a urinary catheter should be used. For example, they cannot be placed on the floor or on top of a bed, hung above the level of the patient's bladder or in a manner that would cause crimping or kinks in a catheter's drainage tubing and therefore impede the patient's use of the catheter, and they must not overly impede a patient mobility. These restrictions result in the need for a urinary catheter, when it is being hung, to utilize a multi-purpose fastener that can safely and conveniently affix to any number of objects (e.g., the rectangular edge of a table top or one of the round legs that support the table) that come into the environment of a patient as he/she moves from one location to another and assumes different positions (i.e., sitting, standing or lying down).

Unfortunately, the fasteners that are today used with urinary catheters cannot meet the diverse attachment requirements that are encountered by patients that use a urinary catheter. The consequence of this can have significant adverse health effects upon a patient since the inability of a urinary catheter to hang properly can cause for the patient obstructions or urinary tract infections.

Accordingly, there exists a need for an adjustable fastener that will allow a catheter bag to be attached to one of a multitude of structural members (e.g., around the vertical leg of a chair or table) in the vicinity of a temporarily stationary, catheter-bag-using patient and such that the attached bag's centerline is oriented vertically.

SUMMARY OF THE INVENTION

Recognizing the need for an improved, adjustable fastener will allow a catheter bag to be attached: (i) to any one of a multitude of structural members in the vicinity of a temporarily stationary, catheter-bag-using patient, and (ii) so that the catheter bag hangs from the fastener in an orientation which places the bag's centerline vertically, the present invention is generally directed to providing such an improved fastener.

In a preferred embodiment, the present invention is such an improved, adjustable fastener that includes: (a) a slide bar having a distal and a proximal end and a slide bar centerline therebetween, (b) a movable jaw attached to the slide bar distal end which has a free end with a movable jaw contact surface that is oriented such that a line perpendicular to the movable jaw contact surface is parallel to the slide bar's centerline, (c) a grip assembly having a front and a rear end and a passageway therebetween that is adapted to allow the slide bar proximal end to pass through the passageway so that a portion of the slide bar is situated within the grip assembly passageway and the slide bar distal end can be situated at any one of a plurality of specified distances in front of the grip assembly front end, (d) a fixed jaw affixed to the grip assembly which has a free end with a fixed jaw contact surface that is oriented such that a line perpendicular to the fixed jaw contact surface aligns with the similar line that is perpendicular to the movable jaw contact surface so that these jaws can come together to clamp a structural member between their contact surfaces when the distance that the slide bar distal end is located from the grip assembly front end is the required amount needed to provide this clamping, (e) a biasing assembly attached to the grip assembly and the slide bar that couples them together in such a manner as to apply a prescribed biasing pressure between the contact surfaces that is sufficient to temporarily adhere them to a structural member when the fastener's jaws are brought together the required distance to temporarily clamp this structural member, and (f) a hook pivotably attached to the slide bar distal end and which has a first leg with a free end, a linking section, and a second leg with a free end that has attached thereto a protuberance, and wherein the first and second legs have prescribed lengths, orientations and a specified distance between them, and with the length of the second leg being greater than that of the first leg, and the orientation of the second leg with respect to the first leg being such that the second leg is angled inward towards the first leg so that the distance between them diminishes as the distance from the linking section towards the free ends increases.

This embodiment may further include a locking connector that attaches to the slide bar distal end and the hook, and wherein this locking connector has a configuration adapted to lock the angular orientation of the hook with respect to the orientation of the fastener's contact surfaces so that, when the adjustable fastener is temporarily clamped to a structural member, the angular orientation of the hook is such that it promotes the catheter bag staying securely attached to the fastener.

Furthermore, the configuration of the locking connector may be further adapted to limit the angular orientations that the hook can take with respect to the fastener's contact surfaces to a plurality of incremental angular orientations so as to enhance the locking capability of this connector.

Additionally, the hook's protuberance typically has a characteristic size that is greater than the characteristic width of the hook's second leg so as to further promote the adherence of the catheter bag to the fastener.

Thus, there has been summarized above (rather broadly and understanding that there are other preferred embodiments which have not been summarized above) the present invention in order that the detailed description that follows may be better understood and appreciated.

DESCRIPTION OF THE PREFERRED EMBODIMENT

Figure 1:
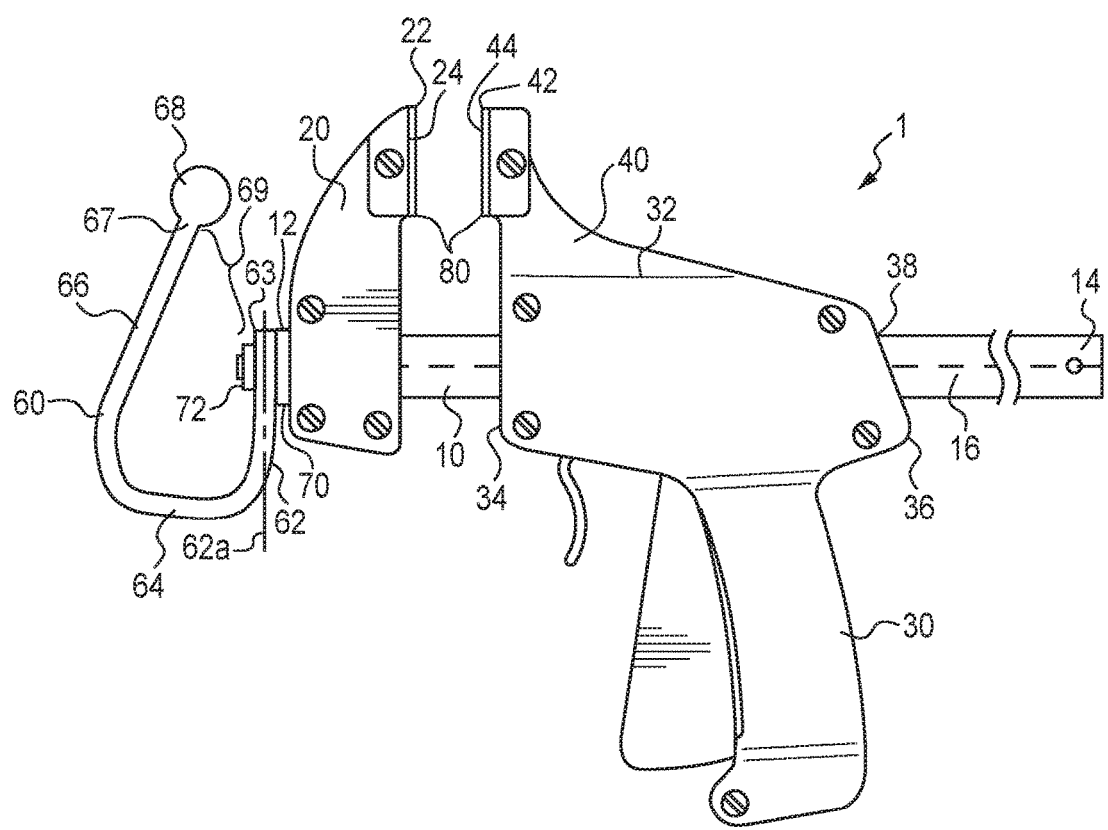
FIG. 1 is a front view, schematic illustration of the present invention.

Before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

The present invention generally relates to an improved adjustable fastener that allows a catheter bag to be attached to any one of a multitude of structural members in the vicinity of a temporarily stationary, catheter-bag-using patient. Additionally, this fastener also allows a catheter bag to hang in a manner that places the catheter bag's centerline in a vertical orientation so as to use gravity to assist in the task of collecting a patient's urinary discharge.

Figure 2:
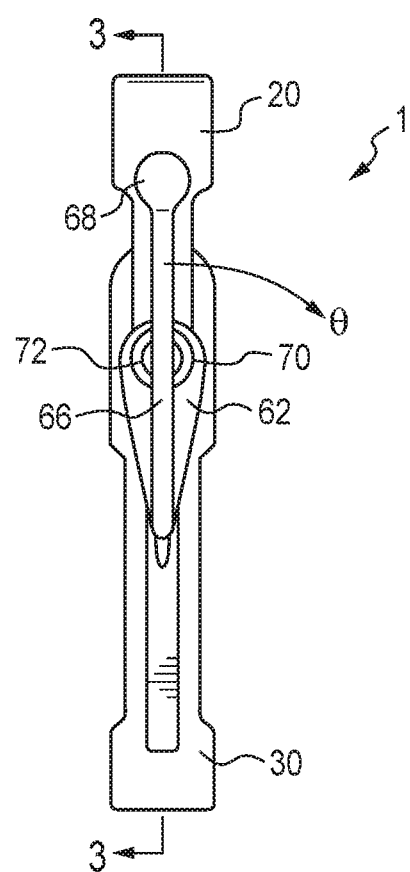
FIG. 2 is a left side view, schematic illustration of the present invention.
Figure 4:
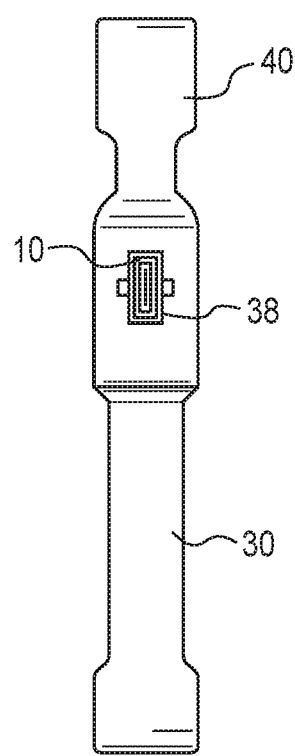
FIG. 4 is a right side view, schematic illustration of the present invention.
Figure 4A:
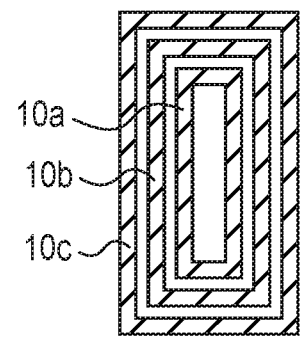
FIG. 4A is a cross-sectional view, schematic illustration of the invention's slide bar taken near its proximal end which shows that it is composed of various telescoping sections.

FIGS. 1 and 2 are schematic illustrations (front and left side views respectively) of the present invention. The improved adjustable fastener 1 of the present invention is seen to include a length-adjustable slide bar 10 that has distal 12 and proximal 14 ends and a slide bar centerline 16 therebetween. To provide this slide bar with an adjustable length, it is composed of telescoping sections 10a, 10b, 10c, etc. that can be extended and then locked into place so increase the length of the slide bar by discrete amounts (i.e., the length of the individual sections that are extended). This feature is provided to avoid the bar's proximal end 14 extending so far from the fastener's grip assembly 30 that it becomes a safety concern or hazard by being a readily accessible, unshielded sharp edge on which one working in the vicinity of the fastener could be cut or otherwise injuried by coming into contact with this proximal end 14. To further avoid this hazard, the configuration of the grip assembly (e.g., the length between its front 34 and rear 36 ends) itself is adapted to minimize the portion of the slide bar proximate its proximal end that extends beyond the grip assembly's rear end. For example, the distance between the grip assembly's front and rear ends can be set to six inches—this will allow six inches of the slide bar to be covered and protected by the grip assembly while also allowing for the jaws 20, 40 of the grip assembly to be spaced apart for distances of up to four or more inches. Such separation distances are sufficient to allow for the grip assembly's attachment to most of the surfaces on which the grip assembly will be used. It is only for the larger separation distances that one would need to extend the grip assembly's telescoping sections 10a, 10b, 10c, etc. See FIGS. 4 and 4A.

A movable jaw 20 is attached to the slide bar's distal 12 end. This movable jaw has a free end 22 with a movable jaw contact surface 24 that is oriented such that a line perpendicular to this contact surface (i.e., a surface normal) is oriented parallel to the slide bar's centerline 16.

A grip assembly 30 is slidably connected to the slide bar. This grip assembly has a top portion 32 and front 34 and rear 36 ends and a passageway 38 that extends between these ends. This passageway and the grip assembly in general is adapted to allow the slide bar's proximal end 14 to pass or slide through the passageway 38 so that a portion of the slide bar is situated within this passageway in such a manner that the grip assembly can be firmly secured to the slide bar. Because the grip assembly is slidably mounted on the slide bar, the slide bar's distal end and consequently the location of the movable jaw's contact surface 24 can be situated at any one of a plurality of specified distances in front of the grip assembly front end 34. It is by adjusting this distance that this fastener can be clamped around a structural member (e.g., around the vertical leg of a chair or table).

A fixed jaw 40 is affixed to the grip assembly's top portion and this fixed jaw has a free end 42 with a fixed jaw contact surface 44 that is oriented such that a line perpendicular to the fixed jaw's contact surface 44 aligns with the comparable line perpendicular to movable jaw's contact surface 24 so that these jaws can come together to clamp a structural member when the distance that the slide bar's distal end 12 is located from the grip assembly's front end 34 is the required amount needed to provide the necessary contact surface spacing for the desired clamping.

To protect the surface of any structural member to which this adjustable fastener is clamped and to enhance its ability to clamp to structural members that do not have flat, planar surfaces, a pad of resilient and compressible material 80 is attached to each of the jar's contact surfaces 24, 44. There are a number of closed cell, foam tapes that are suitable as pad material. Such foam tapes are widely used for a myriad of bonding, sealing, acoustical, and vibration damping applications. With their closed-cell foam structure, they resist air, water, vapor and are not adversely affected by weather and can be easily cleaned and sanitized.

Figure 3:
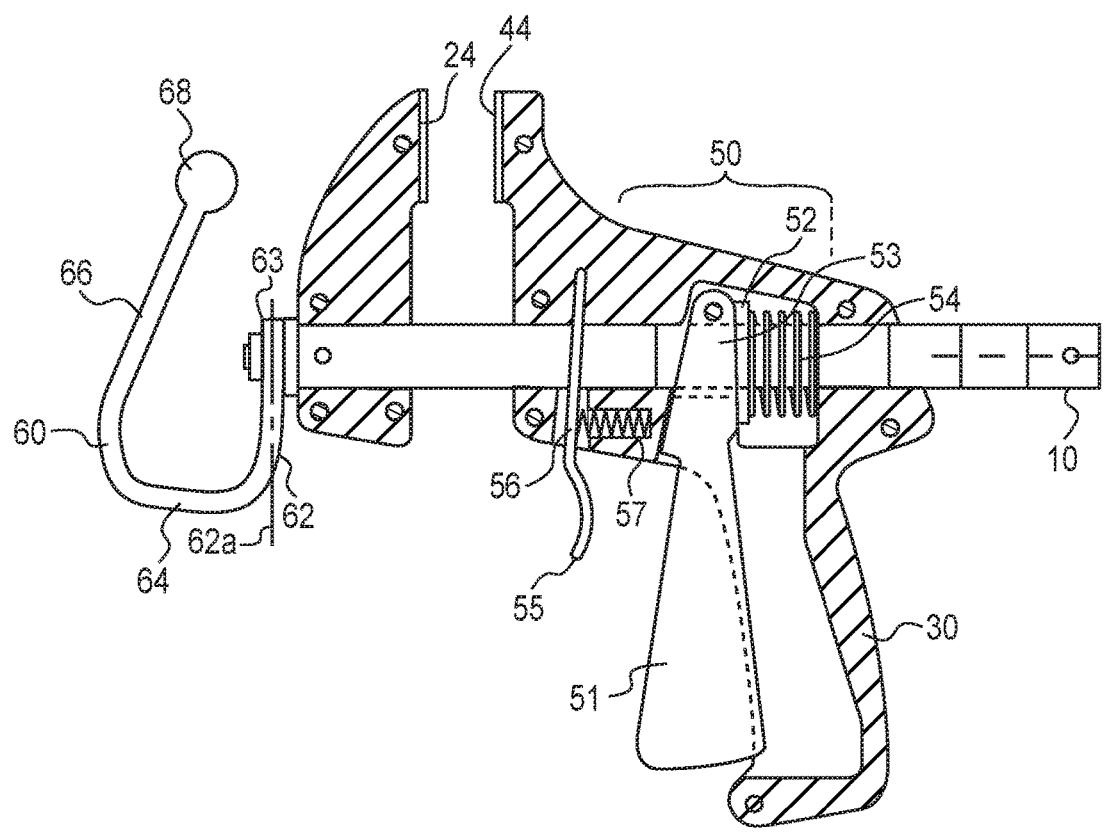
FIG. 3 is a sectional view taken along the lines 3-3 in FIG. 2 of the present invention.

A biasing assembly 50 is attached to the grip assembly 30 and the slide bar 10 and couples the grip assembly and the slide bar together in such a manner as to apply a desired biasing pressure between the jaws' contact surfaces 24, 44 that is sufficient to temporarily adhere the contact surfaces to a structural member that lies between the contact surfaces when they are brought together the required distance to temporarily clamp the structural member. See sectional view FIG. 3. This biasing assembly includes a pivoting trigger handle 51, a trigger handle drive lever 52 and the upper end 53 of the trigger handle which biases against a trigger handle spring 54, a pivoting brake lever 55 with an intermediate point 56 that biases against a brake lever spring 57. Such biasing assemblies for slide bar clamps are well know in the art and therefore there is no need to describe them in any greater detail herein.

A hook 60 is pivotably attached to the slide bar's distal end. This hook has a first leg 62 with a longitudinal centerline 62a and a free end 63, a linking section 64 and a second leg 66 that is located further from the slide bar's distal end 12. The first leg is pivotably attached to the slide bar distal end so that the longitudinal centerline of the first leg is perpendicular to the slide bar's centerline 16. At the free end 67 of the second leg there is a protuberance 68 (e.g., a sphere) that has a characteristic size (e.g., a diameter) that is greater than the characteristic width of the second leg. This second leg is also angled inward towards the first leg such that the distance between them diminishes as the distance upwards from the linking section increases. In general, this hook has a configuration adapted to allow a catheter bag's attachment means to be detachably hung vertically from this hook regardless of the general orientation with respect to gravity of the assembly's contact surfaces. Thus, if these contact surfaces are oriented vertically, the catheter bag's attachment means will hang primarily from the hook's linking section 64. If these contact surfaces are oriented horizontally, the catheter bag's attachment means will hang primarily from the hook's second leg 66, and the hook itself will often be rotated 180 degrees from its orientation shown in FIG. 1 so that the hook's opening 69 is situated away from the contact surfaces 24, 44 and the horizontal structural member to which the fastener is being clamped. The hook's second leg 66 is also seen to be longer than its first leg 62 so as to provide more room and open space around the hook's opening for hanging a catheter bag's attachment means or loop to the hook. The hook's protuberance 68 is seen to be most useful for preventing a catheter bag from slipping off the hook's second leg 66.

A locking connector 70 attaches the hook to the slide bar's distal end and it has a configuration that aids in locking the hook in any desired angular orientation relative to the alignment of the fastener's contact surfaces 24, 44—see FIG. 2 where the angle θ is shown to measure the angular orientation of the hook relative to the contact surfaces. Once the hook is rotated to a desired orientation, a lock nut 72, that attaches to a threaded rod extension from the slide bar's distal end, is used with the connector to lock the hook in its desired angular orientation. In situations where a greater locking capability is needed, the top of the connector and the back side of the first leg which adjoins this connector can be provided with mating ridges that spread radially outward from a center point so as to provide a discrete number of angular orientations. For example, if there were 36 radially outward ridges, the angular orientations available would be in increments of 10 degrees.

The foregoing is considered as illustrative only of the principles of the present invention. Further, since numerous modifications and changes will readily occur to those skilled in the art, it is not desired to limit the invention to the exact construction and operation shown and described herein. Accordingly, all suitable modifications and equivalents may be resorted to, falling within the scope of the invention that is hereafter set forth in the claims to the invention.

I claim:

1. An adjustable fastener for a urinary catheter bag having a top and a bottom end and a longitudinal centerline therebetween and an attachment means affixed to said top end for attaching said bag to one of a multitude of structural members in the vicinity of a patient who is using said bag, wherein the selection of said structural member for the attachment of said bag is based on the requirement that said structural member allows said bag to be situated, when in use, at a position that is below the bladder of said patient, said adjustable fastener comprising:
    a slide bar having a distal and a proximal end and a slide bar centerline therebetween, and wherein the distance between said ends defines the length of said slide bar,
    a movable jaw attached to said slide bar distal end and said movable jaw having a free end with a movable jaw contact surface that is oriented such that a line perpendicular to said movable jaw contact surface is parallel to said slide bar centerline,
    a grip assembly having a top portion and front and rear ends and a passageway therebetween having a configuration adapted to allow a portion of said slide bar proximate said slide bar proximal end to pass threw said passageway so that a portion of said slide bar is situated within said grip assembly passageway and said slide bar distal end is situated at any one of a plurality of specified distances in front of said grip assembly front end, and wherein said grip assembly configuration further adapted to minimize the portion of said slide bar proximate said proximal end that extends beyond said grip assembly rear end,
    a fixed jaw affixed to said grip assembly top portion and said fixed jaw having a free end with a fixed jaw contact surface that is oriented such that a line perpendicular to said fixed jaw contact surface aligns with said line perpendicular to said movable jaw contact surface so that said jaws can come together to clamp a structural member between said contact surfaces when the distance that said slide bar distal end is located from said grip assembly front end is the required amount needed to provide said clamping,
    a biasing assembly attached to said grip assembly and said slide bar that couples said grip assembly and slide bar together in such a manner as to apply a prescribed biasing pressure between said movable and fixed jaw contact surfaces that is sufficient to temporarily adhere said contact surfaces to a structural member that lies between said contact surfaces after said jaws are brought together said required amount to temporarily clamp said structural member,
    a hook having a first leg with a free end, a linking section, and a second leg with a free end that has attached thereto a protuberance, and with said first leg having a longitudinal centerline and wherein said first leg being pivotably attached to said slide bar distal end so that the longitudinal centerline of said first leg is perpendicular to said slide bar centerline, and
    wherein said first and second legs having prescribed lengths, orientations and a specified distance therebetween, and with the length of said second leg being greater than the length of said first leg, and the orientation of said second leg with respect to said first leg being such that said second leg is angled inward towards said first leg so that said distance between said legs diminishes as the distance from said linking section towards the free ends of said legs increases.

2. The adjustable fastener as recited in claim 1, further comprising:
    a locking connector attached to said slide bar distal end and said hook, wherein said locking connector having a configuration adapted to lock the angular orientation of said hook with respect to the orientation of said contact surfaces so that, when said adjustable fastener is temporarily clamped to said structural member, the angular orientation of said hook is such that said orientation promotes said bag attachment means staying securely attached to said hook.

3. The adjustable fastener as recited in claim 2, wherein:
    said configuration of said locking connector further adapted to limit the angular orientations that said hook can take with respect to said contact surfaces to a plurality of incremental angular orientations so as to enhance the locking capability of said locking connector.

4. The adjustable fastener as recited in claim 1, wherein:
    said second leg having a characteristic width and said protuberance having a characteristic size that is greater than the characteristic width of said second leg.

5. The adjustable fastener as recited in claim 2, wherein:
    said second leg having a characteristic width and said protuberance having a characteristic size that is greater than the characteristic width of said second leg.

6. The adjustable fastener as recited in claim 3, wherein:
    said second leg having a characteristic width and said protuberance having a characteristic size that is greater than the characteristic width of said second leg.

7. The adjustable fastener as recited in claim 1, further comprising:

a pad of resilient, compressible and sanitizable material attached to each of said contact surfaces and wherein each of said pads is configured so as to assist in protecting the surface of any structural member to which said adjustable fastener is clamped and to enhance the ability of said adjustable fastener to clamp to structural members that do not have flat, planar surfaces to which said adjustable fastener can be clamped.

8. The adjustable fastener as recited in claim 2, further comprising:

a pad of resilient, compressible and sanitizable material attached to each of said contact surfaces and wherein each of said pads is configured so as to assist in protecting the surface of any structural member to which said adjustable fastener is clamped and to enhance the ability of said adjustable fastener to clamp to structural members that do not have flat, planar surfaces to which said adjustable fastener can be clamped.

9. The adjustable fastener as recited in claim 3, further comprising:

a pad of resilient, compressible and sanitizable material attached to each of said contact surfaces and wherein each of said pads is configured so as to assist in protecting the surface of any structural member to which said adjustable fastener is clamped and to enhance the ability of said adjustable fastener to clamp to structural members that do not have flat, planar surfaces to which said adjustable fastener can be clamped.

10. The adjustable fastener as recited in claim 4, further comprising:

a pad of resilient, compressible and sanitizable material attached to each of said contact surfaces and wherein each of said pads is configured so as to assist in protecting the surface of any structural member to which said adjustable fastener is clamped and to enhance the ability of said adjustable fastener to clamp to structural members that do not have flat, planar surfaces to which said adjustable fastener can be clamped.

11. The adjustable fastener as recited in claim 5, further comprising:

a pad of resilient, compressible and sanitizable material attached to each of said contact surfaces and wherein each of said pads is configured so as to assist in protecting the surface of any structural member to which said adjustable fastener is clamped and to enhance the ability of said adjustable fastener to clamp to structural members that do not have flat, planar surfaces to which said adjustable fastener can be clamped.

12. The adjustable fastener as recited in claim 6, further comprising:

a pad of resilient, compressible and sanitizable material attached to each of said contact surfaces and wherein each of said pads is configured so as to assist in protecting the surface of any structural member to which said adjustable fastener is clamped and to enhance the ability of said adjustable fastener to clamp to structural members that do not have flat, planar surfaces to which said adjustable fastener can be clamped.

13. The adjustable fastener as recited in claim 1, wherein:
said slide bar having a configuration that enables said length of said slide bar to be adjustable so as to allow said proximal end of said slide bar to stay in close proximity to said rear end of said grip assembly.

14. The adjustable fastener as recited in claim 2, wherein:
said slide bar having a configuration that enables said length of said slide bar to be adjustable so as to allow said proximal end of said slide bar to stay in close proximity to said rear end of said grip assembly.

15. The adjustable fastener as recited in claim 3, wherein:
said slide bar having a configuration that enables said length of said slide bar to be adjustable so as to allow said proximal end of said slide bar to stay in close proximity to said rear end of said grip assembly.

16. The adjustable fastener as recited in claim 4, wherein:
said slide bar having a configuration that enables said length of said slide bar to be adjustable so as to allow said proximal end of said slide bar to stay in close proximity to said rear end of said grip assembly.

17. The adjustable fastener as recited in claim 5, wherein:
said slide bar having a configuration that enables said length of said slide bar to be adjustable so as to allow said proximal end of said slide bar to stay in close proximity to said rear end of said grip assembly.

18. The adjustable fastener as recited in claim 6, wherein:
said slide bar having a configuration that enables said length of said slide bar to be adjustable so as to allow said proximal end of said slide bar to stay in close proximity to said rear end of said grip assembly.

19. The adjustable fastener as recited in claim 7, wherein:
said slide bar having a configuration that enables said length of said slide bar to be adjustable so as to allow said proximal end of said slide bar to stay in close proximity to said rear end of said grip assembly.

20. The adjustable fastener as recited in claim 8, wherein:
said slide bar having a configuration that enables said length of said slide bar to be adjustable so as to allow said proximal end of said slide bar to stay in close proximity to said rear end of said grip assembly.

\* \* \* \* \*